(12) United States Patent
Yokota et al.

(10) Patent No.: US 7,165,837 B2
(45) Date of Patent: Jan. 23, 2007

(54) SWIMMING GOGGLES

(75) Inventors: Takeshi Yokota, 2-14-14-201 Sakuragawa, Itabashi-ku, Tokyo (JP) 174-0075; Keiko Yokota, 2-14-14-201 Sakuragawa, Itabashi-ku, Tokyo (JP) 174-0075

(73) Assignees: Takeshi Yokota, Tokyo (JP); Keiko Yokota, Tokyo (JP)

( * ) Notice: Subject to any disclaimer, the term of this patent is extended or adjusted under 35 U.S.C. 154(b) by 90 days.

(21) Appl. No.: 10/533,185

(22) PCT Filed: Nov. 8, 2002

(86) PCT No.: PCT/JP02/11673

§ 371 (c)(1),
(2), (4) Date: Apr. 28, 2005

(87) PCT Pub. No.: WO2004/041369

PCT Pub. Date: May 21, 2004

(65) Prior Publication Data

US 2006/0010587 A1    Jan. 19, 2006

(51) Int. Cl.
*G02C 1/00* (2006.01)
(52) U.S. Cl. .............................. 351/43; 351/45; 351/46; 2/426
(58) Field of Classification Search .................. 351/43, 351/44, 45, 46, 41, 158, 156, 157; 2/426, 2/431, 433, 440
See application file for complete search history.

(56) References Cited

U.S. PATENT DOCUMENTS 3,672,750 A * 6/1972 Hagen .......................... 351/43

FOREIGN PATENT DOCUMENTS

| JP | H10-290846 | 11/1998 |
| JP | 3075386 | 2/2001 |

* cited by examiner

*Primary Examiner*—Hung Xuan Dang
(74) *Attorney, Agent, or Firm*—Akerman Senterfitt; Stephan Pendorf; Yonghong Chen

(57) ABSTRACT

This invention provides swimming goggles that improve the field of vision, and particularly improve the field of vision while swimming.

The eye cup 2 comprises: a contact section that comes in contact with the area surrounding the eye; a peripheral section 6 that is located around that contact section and that, when worn, extends a specified distance forward in the viewing direction; and a forward-viewing section 7 that is arranged such that the bottom is located on the front end section of the bottom of the peripheral section 6, and the top is located on or near the aforementioned contact section. Also, a difficult-viewing section 14 is located at least at the bottom part of the peripheral section 6 below the center position of the forward-viewing section 7 such that it is more difficult to see through than the top portion of the forward-viewing section 7, which makes it possible to improve the field of vision as well as makes it possible to swim without sensing the light refraction.

17 Claims, 16 Drawing Sheets

SWIMMING GOGGLES

CROSS REFERENCE TO RELATED APPLICATION

This application is a national stage of PCT/JP2002/011673 filed Nov. 8, 2002 under the International Convention.

BACKGROUND OF THE INVENTION

1. Field of the Invention

This invention relates to swimming goggles, and more particularly to swimming goggles that are most suitable to competitive swimming.

2. Description of the Related Art

Swimming goggles cover just the eyes and protect the eyes, as well as create a space in front of the eyes and adjust the focal point of the eyes. For human eyes, not having space in front of the eyes makes it impossible to adjust the focal point, and when the eyes are open underwater, everything is blurred and difficult to see.

Typical swimming goggles comprise a pair of eyecups that are connected by a connecting belt, and a belt for wearing the goggles that is fastened between both ends of the eyecups.

The aforementioned pair of eye cups maintains a space in front of each of the eyes, and when worn, are formed of a single piece of transparent plastic such that a flat forward-viewing section that is nearly orthogonal to the direction of the forward line of vision is joined to the forward end section of a cylindrical-shaped peripheral section that extends in the direction of the forward line of vision. By keeping this forward-viewing section at a specified location separated from the eyes by the cylindrical peripheral section, the forward field of vision is in a direction perpendicular to the flat forward-viewing section, which is good. However, when swimming crawl in particular, the eyes are looking upward to look in the direction of swimming. In this case, the field of vision is not in a direction perpendicular to the forward-viewing section, but is at an angle, so the swimmer may sense the light refraction, and it is possible that the field of vision will become poor.

Therefore, the inventors, first proposed swimming goggles having eye cups in which the length of the top part of the peripheral section in the direction of the field of vision was made shorter than the other parts of the peripheral section, and the flat forward-viewing section was such that the top side was tilted in the direction toward the rear of the field of vision. Since the forward-viewing section is tilted, when the eyes are looking upward, the field of vision is in a direction that is perpendicular or nearly perpendicular to the forward-viewing section. Therefore, it is possible to swim without sensing the light refraction or being bothered by the light refraction, thus improving the field of vision.

When wearing these swimming goggles and swimming crawl, the swimmer swims looking forward with the eyes just looking upward, so the field of vision is good. However, when swimming with an up and down motion such as in the breaststroke or butterfly, it is possible that the swimmer will swim looking in both the direction of the forward-viewing section and the direction of the bottom part of the peripheral section. When looking at the forward-viewing section and bottom of the peripheral section at the same time, or when looking at the border between those two sections, the light refraction in the forward-viewing section and the bottom of the peripheral section is different, so what is seen is different. For example, when looking through the bottom of the peripheral section, refracted light is sensed and what is seen appears to be more curved than what is seen from the forward-viewing section. Therefore, two images are seen having different degrees of curvature, and it is possible that the swimmer will begin to feel dizzy or nauseous.

SUMMARY OF THE INVENTION

Taking into consideration these circumstances, the object of this invention is to provide swimming goggles that improve the field of vision as well as make it possible to swim without feeling light refraction.

In order to accomplish the aforementioned object, the swimming goggles of this invention are swimming goggles having a pair of left and right eye cups and where each eye cup comprises: a contact section that comes in contact with the area surrounding the eye; a peripheral section that is located around that contact section and that, when worn, extends a specified distance forward in the viewing direction; and a forward-viewing section that is arranged on that peripheral section; and where the length in the viewing direction of the top part of the aforementioned peripheral section is formed such that it is shorter than the other parts of the peripheral section; and a difficult-viewing section is located at least at the bottom part of the aforementioned peripheral section below the center position of the aforementioned forward-viewing section such that it is more difficult to see through than the top portion of the forward-viewing section.

Also, the swimming goggles of this invention are swimming goggles having a pair of left and right eye cups where each eye cup comprises: a contact section that comes in contact with the area surrounding the eye; a peripheral section that is located around that contact section and that, when worn, extends a specified distance forward in the viewing direction; and a forward-viewing section that is arranged on that peripheral section; and where the top end section of the forward-viewing section is formed such that it is located near the aforementioned contact section; and a difficult-viewing section is located at least at the bottom part of the aforementioned peripheral section below the center position of the aforementioned forward-viewing section such that it is more difficult to see through than the top portion of the forward-viewing section.

Moreover, the swimming goggles of this invention are swimming goggles having a pair of left and right eye cups where each eye cup comprises: a contact section that comes in contact with the area surrounding the eye; a peripheral section that is located around that contact section and that, when worn, extends a specified distance forward in the viewing direction; and a forward-viewing section that is arranged on that peripheral section; and where the top end section of the forward-viewing section is directly connected to the aforementioned contact section; and a difficult-viewing section is located at least at the bottom part of the aforementioned peripheral section below the center position of the aforementioned forward-viewing section such that it is more difficult to see through than the top portion of the forward-viewing section.

It is preferred that the aforementioned forward-viewing section comprises: a vertical section that extends a specified distance upward from the bottom end section to a position below the center position; and a main-viewing section that is inclined from the vertical section backward from the viewing direction to or near the aforementioned contact section.

It is preferred that the border between the aforementioned vertical section and aforementioned main-viewing section be curved.

It is preferred that the aforementioned forward-viewing section be formed into a curved shape.

It is preferred that the border between the aforementioned peripheral section and aforementioned forward-viewing section be curved.

It is preferred that the aforementioned difficult-viewing section be located on all or part of the aforementioned vertical section.

It is preferred that the aforementioned difficult-viewing section be formed by using coloring, patterning, graphic images, text, gradation, mesh shading, mirror coating, texturing, semi-transparency or a combination of these.

It is preferred that the aforementioned difficult-viewing section be formed using coloring, and the aforementioned forward-viewing section be formed such that it is the same color as or a different color than the aforementioned difficult-viewing section, and that the color be easier to see through than that of the aforementioned difficult-viewing section.

The difficult-viewing section can also be such that it is colored and that the aforementioned forward-viewing section be transparent.

Also, it is possible that when forming the eye cup with a mold, the color of the aforementioned difficult-viewing section and the color of the aforementioned forward-viewing section be formed at the same time.

Moreover, it is possible to form just the aforementioned difficult-viewing section separately, and then fit it over the eyecup.

Furthermore, it is also possible to locate the difficult-viewing section below the center position of the aforementioned forward-viewing section.

Also, it is possible to locate the difficult-viewing section on at least the bottom part of the aforementioned peripheral section.

Moreover, it is also possible for the vertical section to be inclined. The 'inclination' referred to here is the optimum angle for accomplishing the object of this invention.

DESCRIPTION OF THE PREFERRED
EMBODIMENTS OF THE INVENTION

The preferred embodiments of the invention will be described in detail below based on the supplied drawings.

Figure 1:
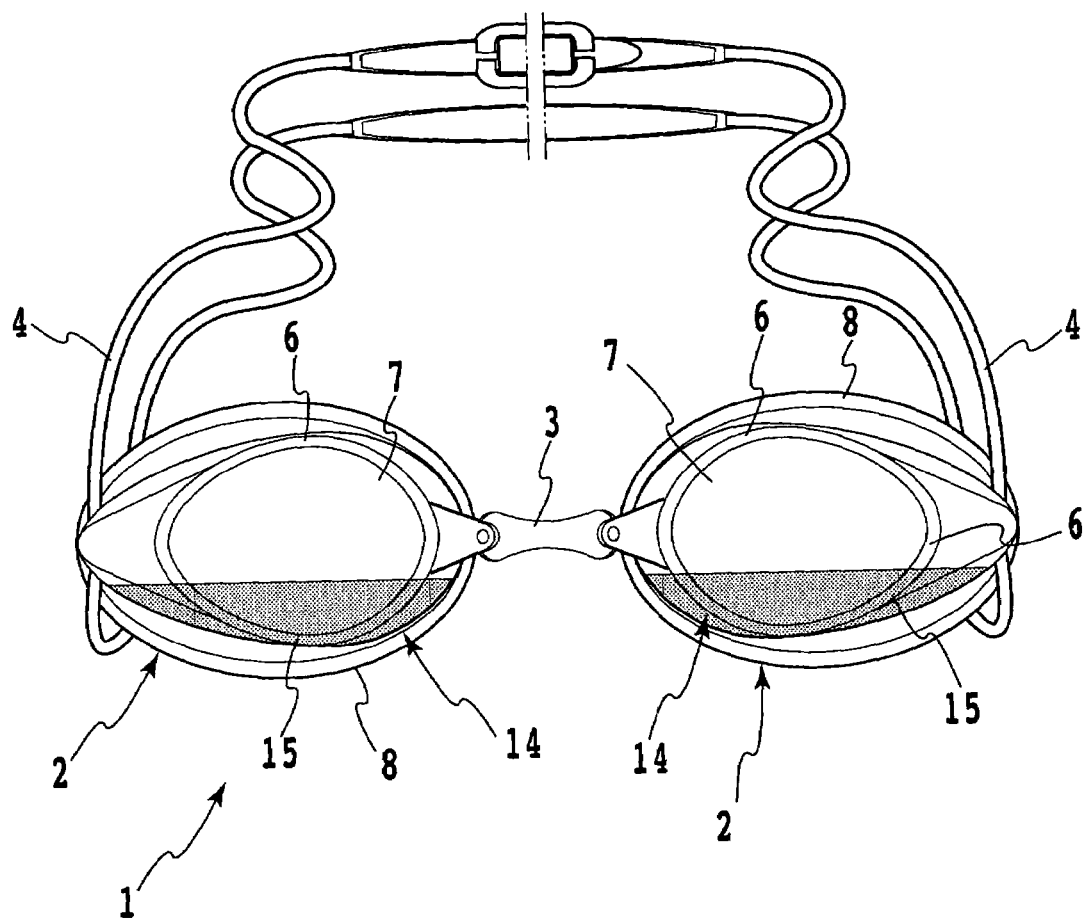
FIG. 1 is a front view showing an example of the swimming goggles of this invention.
Figure 2:
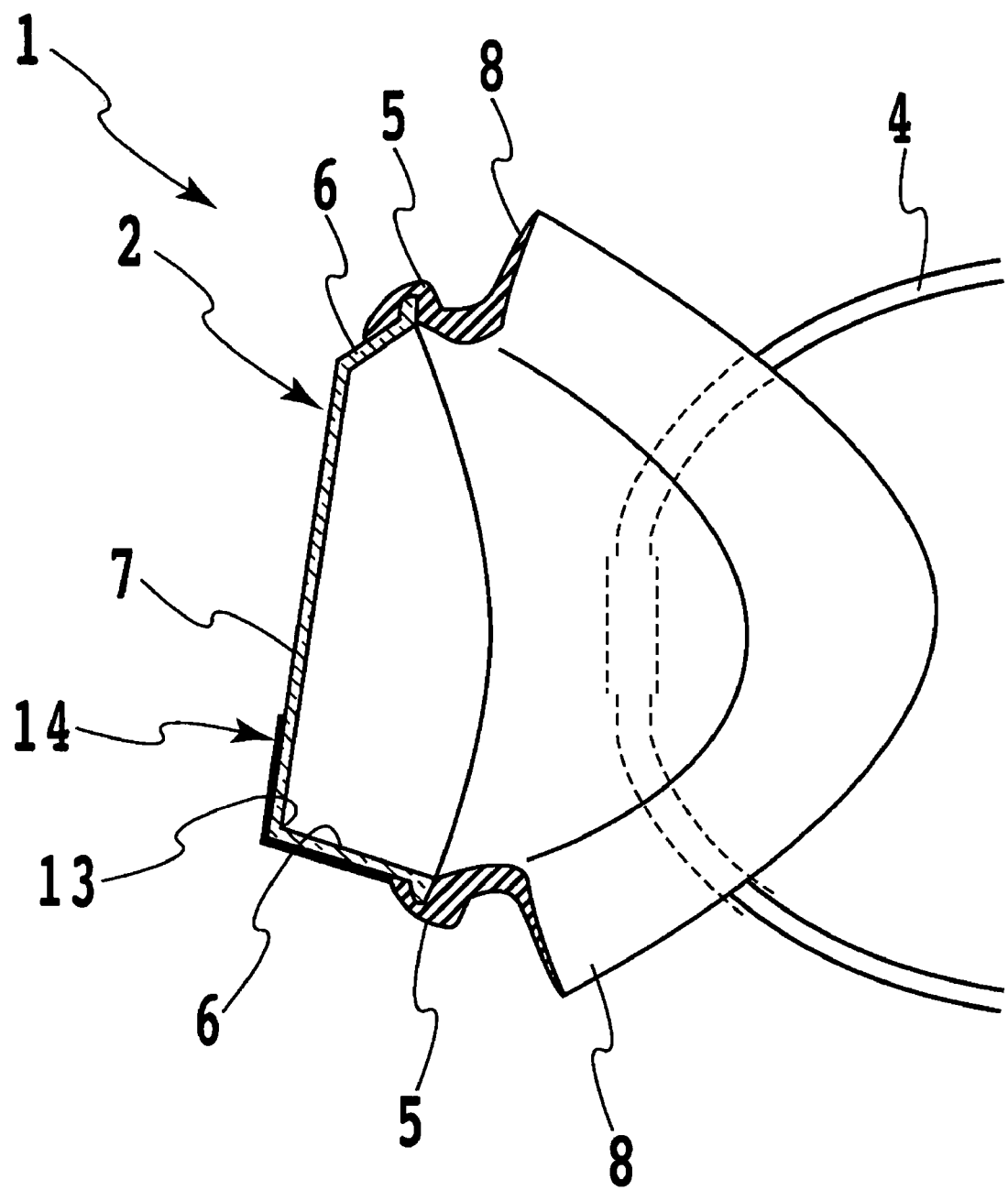
FIG. 2 is a cross-sectional view showing an example of the eyecup of this invention.

FIG. 1 is an example of the swimming goggles of this invention. FIG. 2 is an example of a cross-sectional view of the eyecup of this invention. FIG. 3 thru FIG. 6 is cross-sectional drawings of other examples of the eyecup of this invention.

In FIG. 1 thru FIG. 6, 1 indicates the swimming goggles, and these swimming goggles 1 comprise: a pair of left and right eye cups 2, 2 that cover just the eyes and protect the eyes; a connecting band 3 that connects the pair of eye cups 2, 2; and an adjustable-length support band 4 that is attached to both ends of the connected pair of eye cups 2, 2.

The connecting band 3 is made of a flexible and stretchable material; for example, a soft plastic material such as polyurethane plastic. Also, a connecting band 3 is used that is capable of adjusting the length between the pair of eyecups 2, 2. The support band 4 can be anything as long as its length is adjustable and is stretchable; for example, a band made of a rubber type of stretchable elastic material can be used.

The pair of eye cups 2, 2 each comprises: a contact section 5 that comes in contact with the area around the eye; a peripheral section 6 that is located around that contact section 5, and when worn, extends a specified distance in the forward direction of the field of vision; and a forward-viewing section 7 whose bottom end section is located on the bottom front end section of the peripheral section 6, and whose top section is located on or near the aforementioned contact section 5. The eye cup 2 can be made into one piece using transparent plastic such as cellulosic plastic, acrylic plastic, polycarbonate, or the like, or can be made such that just the forward-viewing section 7 is made of transparent plastic and the contact section 5 and peripheral section 6 are made of a hard material.

The contact section 5 is formed into a shape such that when it is in contact with the area around the eye, water cannot enter into the eyecup from any gaps. In order to improve the seal and also so that the face around the eye does not hurt, a cushion 8 is placed around the contact section 5. This cushion 8 can be removable when necessary.

Figure 3:
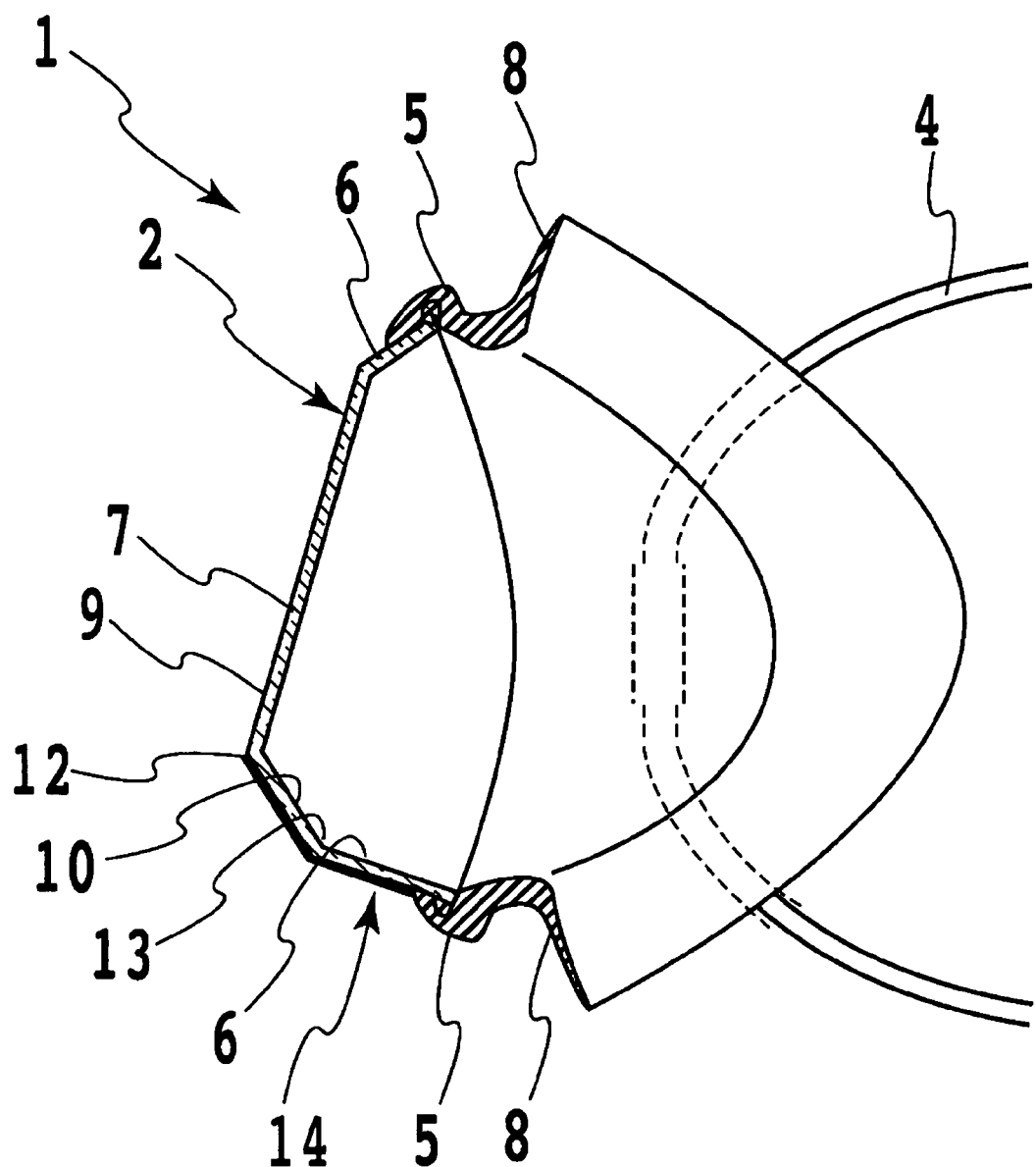
FIG. 3 is a cross-sectional view showing another example of the eyecup of this invention.
Figure 4:
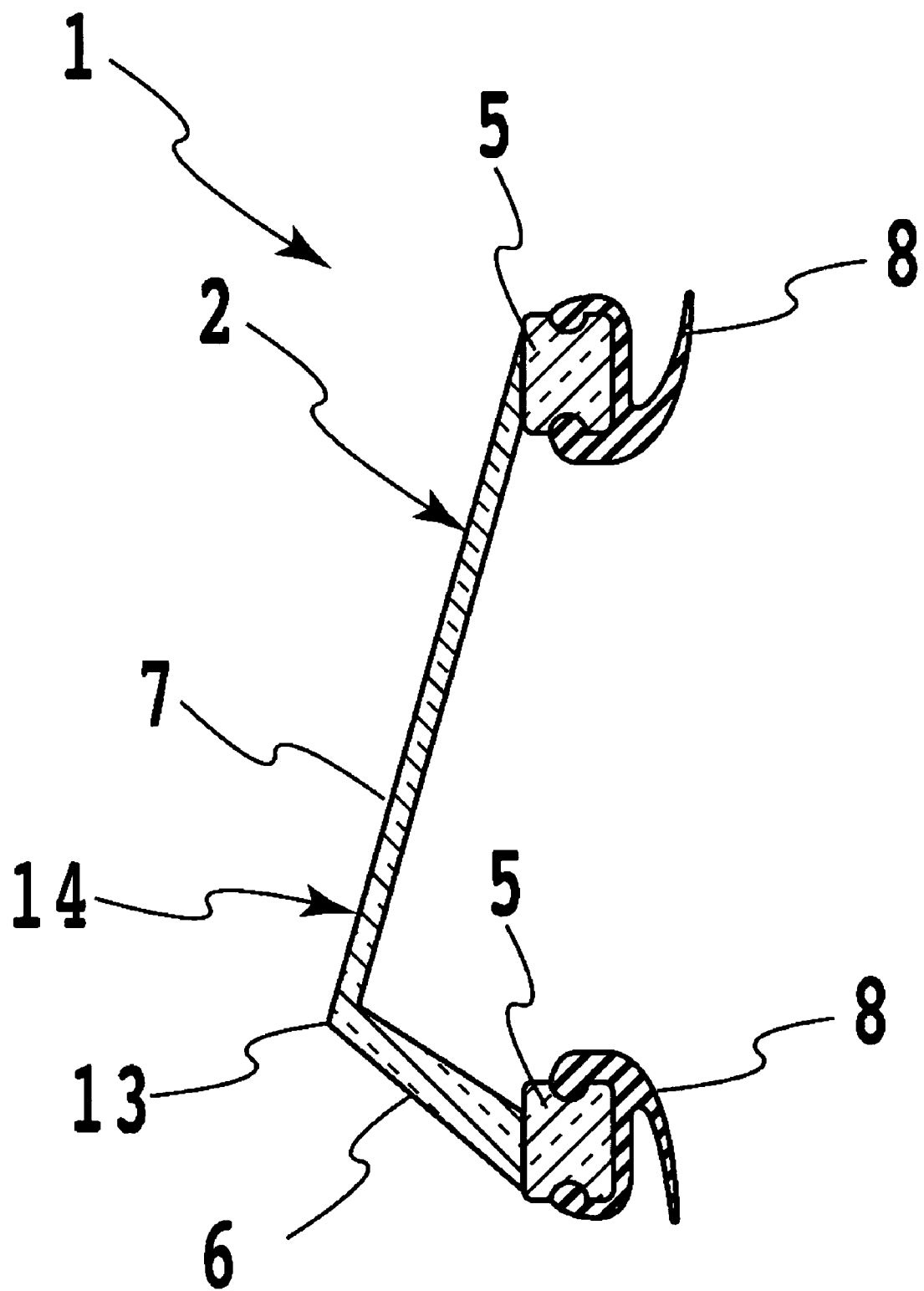
FIG. 4 is a cross-sectional view showing another example of the eyecup of this invention.
Figure 5:
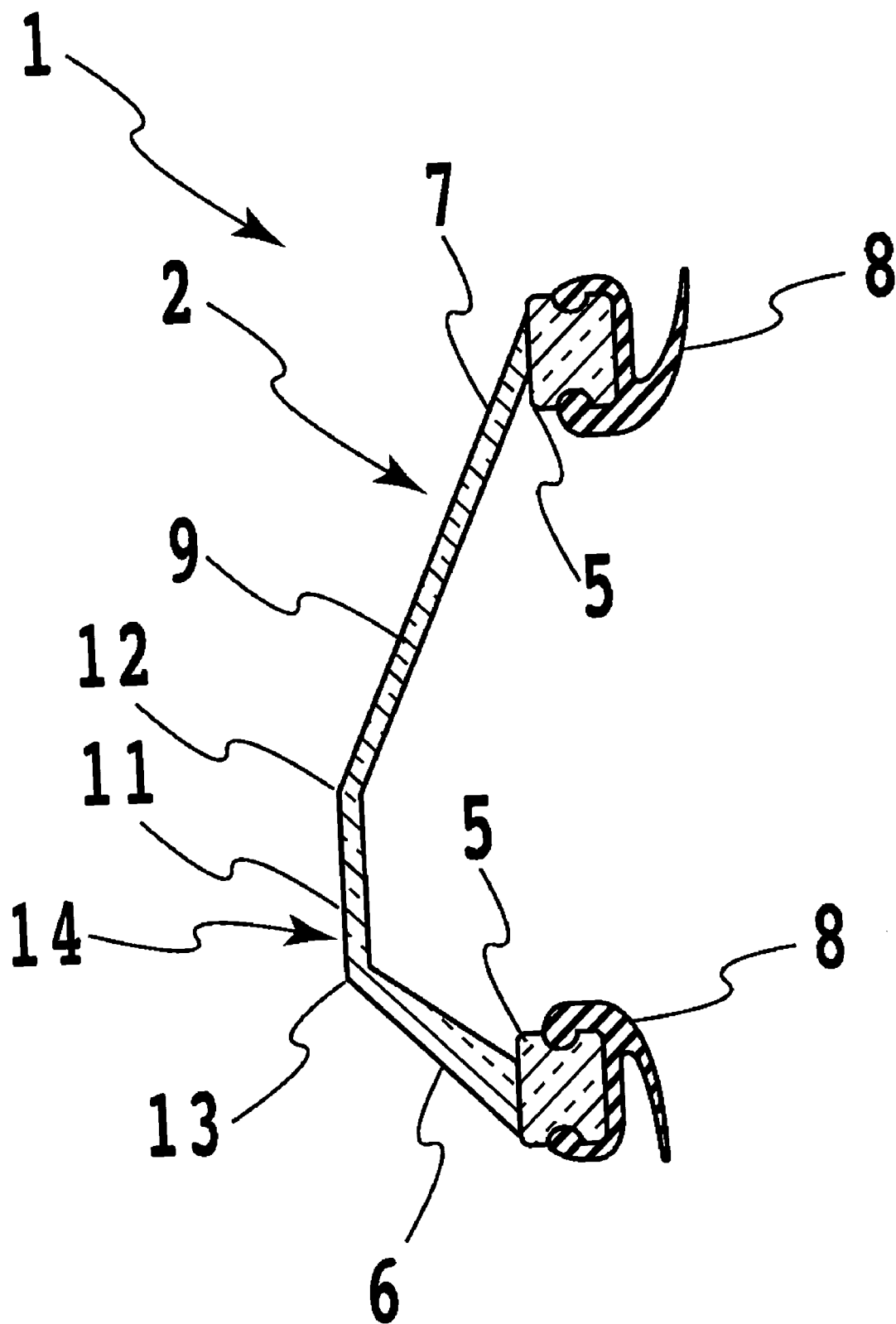
FIG. 5 is a cross-sectional view showing another example of the eyecup of this invention.
Figure 6:
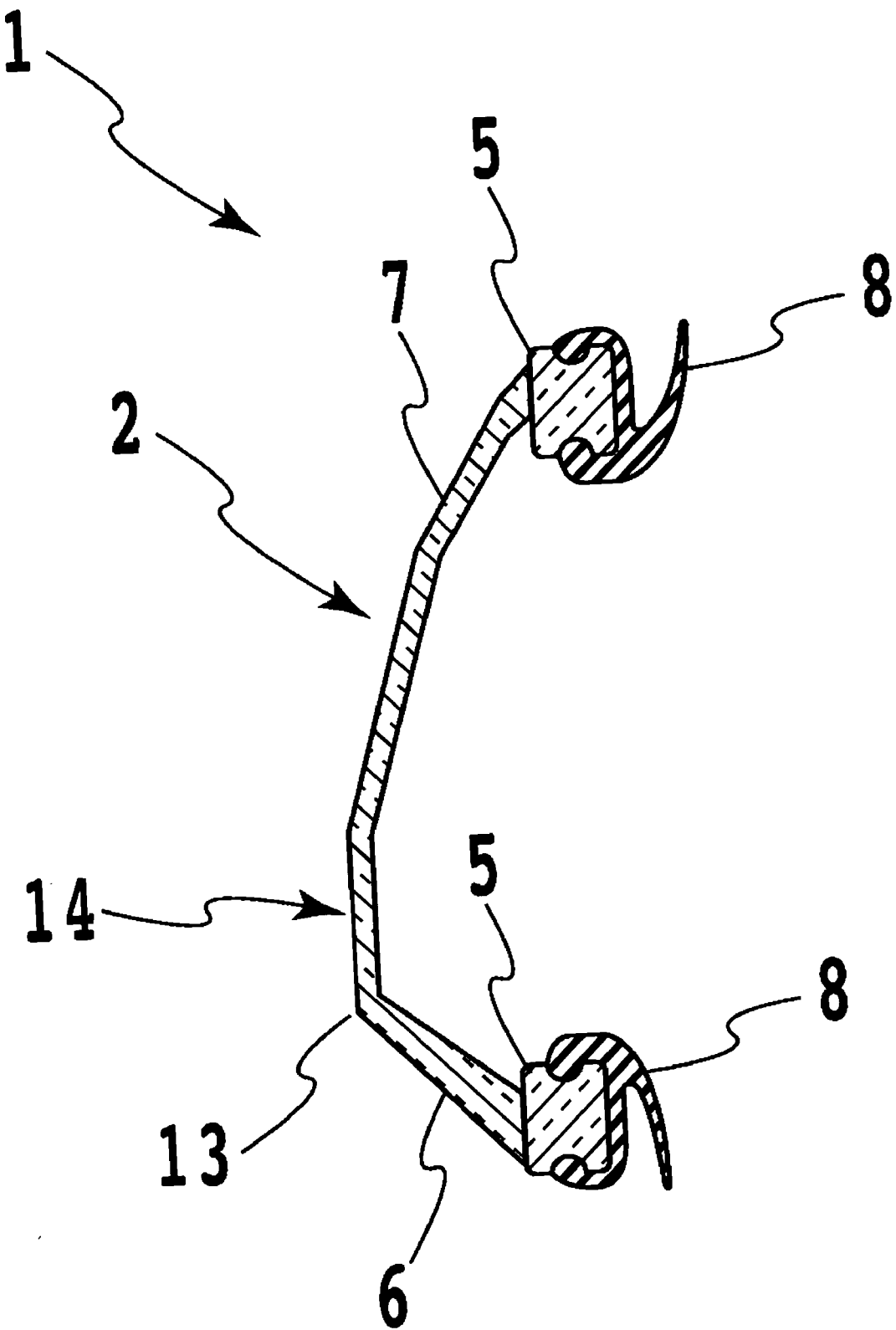
FIG. 6 is a cross-sectional view showing another example of the eyecup of this invention.

The peripheral section 6 is formed such that the contact section 5 is located around one end and the forward-viewing section 7 is located on the other end, and is shaped such that the bottom section and left and right sections extend a specified distance forward in the direction of the field of vision (nearly a cylindrical shape). As shown in FIG. 2 and FIG. 3, the top section of the peripheral section 6 is formed such that its length in the direction of the field of vision is shorter than other parts of the peripheral section 6 (for example the bottom section of the peripheral section 6), and it is particularly preferred that it be extremely short. Moreover, as shown in FIG. 4 thru FIG. 6, the peripheral section 6 can be formed into a shape such that the top end section of the forward-viewing section 7 is connected directly to the contact section 5, and the top section of the peripheral section 6 is done away with. In other words, the top section of the peripheral section 6 to which the top end section of the forward-viewing section 7 is connected is formed shorter than the other parts of the peripheral section 6, or the top end section of the forward-viewing section 7 is connected directly to the contact section 5.

The bottom section, left and right sections and the top section when there is one of the peripheral section 6 can also be formed such that they are parallel with the viewing direction, or can be formed such that they are gradually inclined toward the eye side in the forward viewing direction. Taking into consideration the resistance in the water, it is preferred that they be inclined.

The shape of the forward-viewing section 7 (lens surface) is not particularly limited as long as it extends to or near the contact section 5; for example, as shown in FIG. 2 and FIG. 4, it can be flat, or as shown in FIG. 6, it can be curved.

Also, as shown in FIG. 3, the forward-viewing section 7 (lens surface) can be formed such that it comprises a flat plate-shaped main-viewing section 9 that is inclined from the top end section a specified distance downward in the forward viewing direction, and a flat plate-shaped inclined section 10 that is inclined from the bottom end of that main viewing section 9 to the aforementioned peripheral section (bottom peripheral section) 6 in the backward direction from the viewing direction. Moreover, as shown in FIG. 5, the forward-viewing section 7 (lens surface) can also be formed such that it comprises a flat plate-shaped main-viewing section 9 that is inclined from the top end section a specified distance downward in the forward viewing direction, and a flat plate-shaped vertical section 11 that extends from the bottom end of that main viewing section 9 to the aforementioned peripheral section (bottom of the peripheral section) 6 such that it is nearly orthogonal with the viewing direction.

When the forward-viewing section 7 is formed such that is comprises a main-viewing section 9 and inclined section 10 or vertical section 11 in this way, it is preferred that the border between the main-viewing section 9 and the inclined section 10 or vertical section 1 be formed into a curved shape.

Also, it is preferred that the angle at which the forward-viewing section 7 and main viewing section 9 crosses a plane that is orthogonal to the viewing direction be in the range 0 to 40°. By setting the angle in this way, the range of the viewing angle becomes 31° to 67°, and it is possible to obtain a large attack angle. Incidentally, in the case of conventional swimming goggles, the aforementioned viewing angle is 20° to 41°.

Therefore, the swimmer is able to check in front and swim with little water resistance while at the same time keeping the head as much as possible in a horizontal state.

Moreover, it is preferred that the main-viewing section 9 be formed such that the bottom end section is high with respect to the top end section; and when worn, it is preferred that the border 12 between the aforementioned main-viewing section 9 and inclined section 10 or vertical section 11 be positioned lower than the position of the center of the swimmer's eye, and particularly, it is preferred that the border 12 be formed and set such that it is positioned in the proximity of the bottom eyelid of the swimmer's eye.

This is in order to prevent a difference in actual distance and perceived distance due to light refraction of the main-viewing section 9 of the aforementioned forward-viewing section 7 that occurs in the water when the aforementioned border 12 is at the same level as the viewing direction of the eye.

For example, when the aforementioned border 12 is at the same level as the viewing direction of the eye as described above, objects appear to be located approximately 10 cm closer than the actual distance.

Therefore, touching the wall when performing a quick turn is done too soon, and there is a possibility that it will not be possible to touch the wall properly, in competitive swimming when the race comes down to $1/100$ sec., this could be very crucial.

Also, the more this border 12 is lower than the center of the eye, the more possible it is to keep the error described above to a minimum, and by having it lower than the center of the eye, it does not hinder the field of vision, and it possible to maintain a good field of vision.

Moreover, it is preferred that the border 13 between the bottom end section of the forward-viewing section 7 and the peripheral section 6 be curved. By curving this border 13 in this way, there are no horizontal lines in the forward-viewing section 7, and thus viewing becomes good.

Furthermore, as shown in FIG. 1 thru FIG. 13, a difficult-viewing section 14 from which it is more difficult to see from than the top of the forward-viewing section 7 is located lower than the center of the eye E, or more preferably, lower than the eye E of the swimmer H who is wearing the eye cups 2, 2.

More specifically, as shown in FIG. 2, FIG. 4 and FIG. 6 for example, when this difficult viewing section 14 is formed into a flat plate shape or curved plate shape, it is located at the bottom of the peripheral section 6. It does not necessarily need to be located on the forward-viewing section 7, however, as shown in FIG. 2, FIG. 4 and FIG. 6, it is preferred that it be located from below the eye E of the swimmer H (see FIG. 12) who is wearing the forward-viewing section 7 to the bottom of the peripheral section 6.

Also, as shown in FIG. 3 and FIG. 5, when the forward-viewing section 7 is formed such that it comprises a main-viewing section 9 and inclined section 10 or vertical section 11, it is preferred that the difficult-viewing section 14 be located over the bottom of the peripheral section 6 and part (preferably from the center to the bottom) or all (it is located over all in the examples shown in the figures) of the inclined section 10 or vertical section 11. It is not necessary that it be located on the main-viewing section 9, however, it is preferred that it be located from a position below the eye E of the swimmer H who is wearing the main viewing section 9 to the inclined section 10 or vertical section 11.

The difficult-viewing section 14 is formed such that it is more difficult to see through than the upper portion of the forward-viewing section 7.

Figure 15:
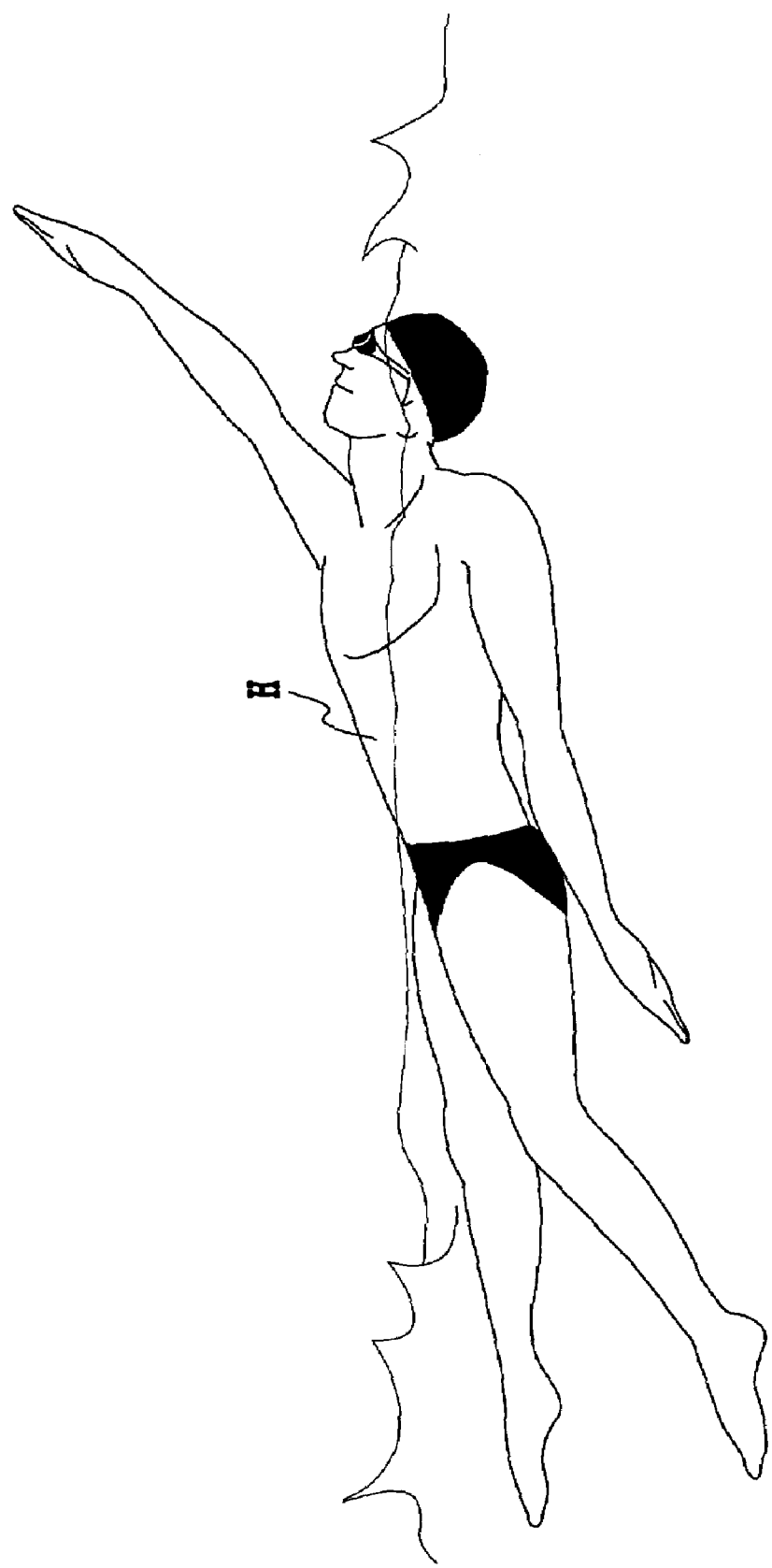
FIG. 15 is a side view showing a swimmer that is swimming backstroke.

Being more difficult to see through than the upper portion of the forward-viewing section 7 referred to in this invention, means for example that it is possible to see enough so that there is no problem on land such as when walking on the pool side, but that it is more difficult to see through than the upper portion of the forward-viewing section 7 when in water or when swimming; for example, it is possible to see (check) the flag lines located above the pool when swimming the backstroke as shown in FIG. 15. The flags are not always set up, however, for example, for a 25-meter pool, they are set up at 5 m, 12.5 m and 20 m, and for a 50-meter pool, they are set up at 5 m, 25 m and 45 m.

The difficult-viewing section 14 can be any shape as long as it is possible to make it more difficult to see through than the upper portion of the forward-viewing section 7; for example, it can be formed such that it is colored, has a pattern, an image, text, gradation, is shaded, has a mirror coating, is textured, or is semi-transparent or a combination of these.

Figure 12:
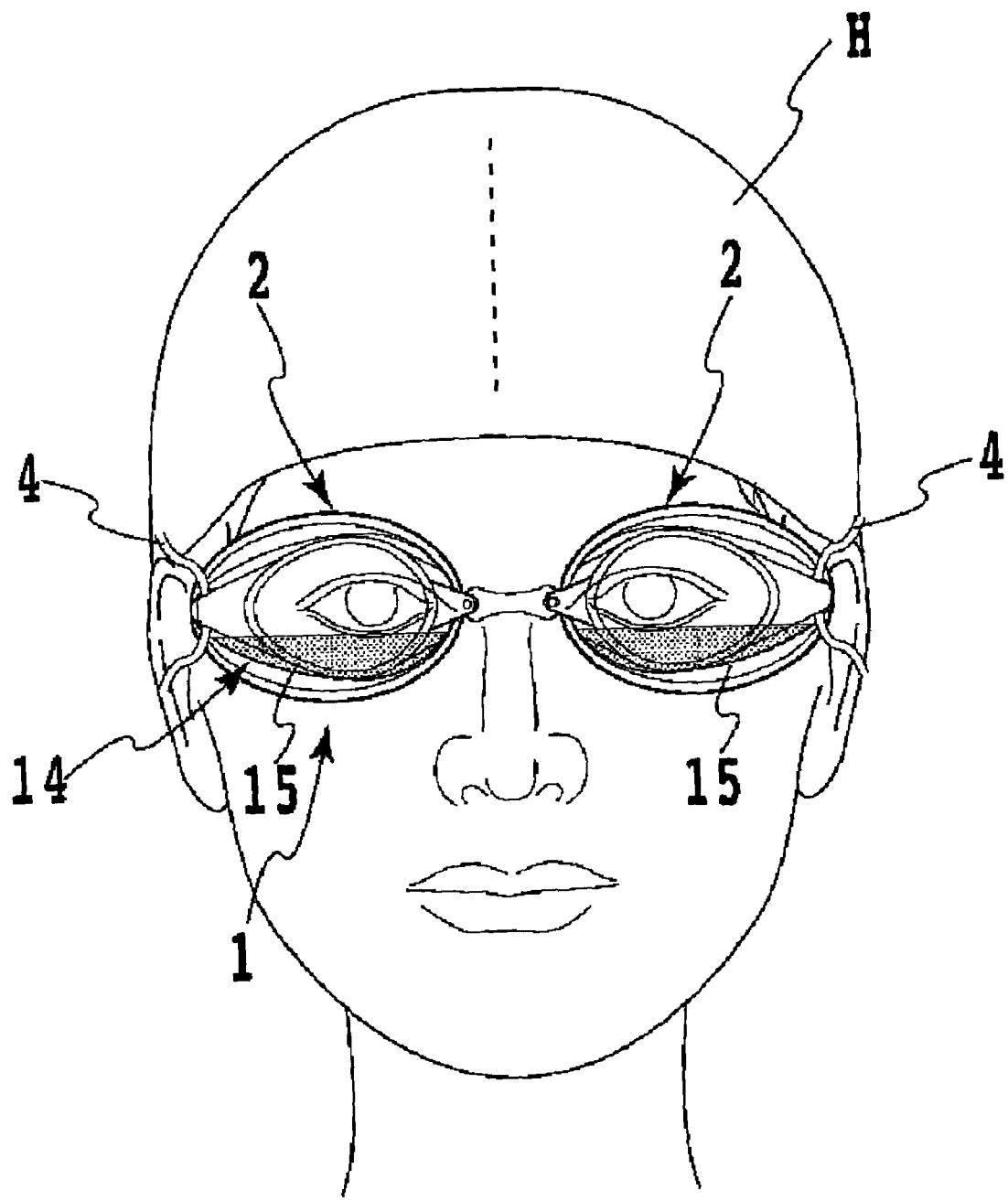
FIG. 12 is a front view showing a swimmer wearing the swimming goggles shown in FIG. 1.
Figure 13:
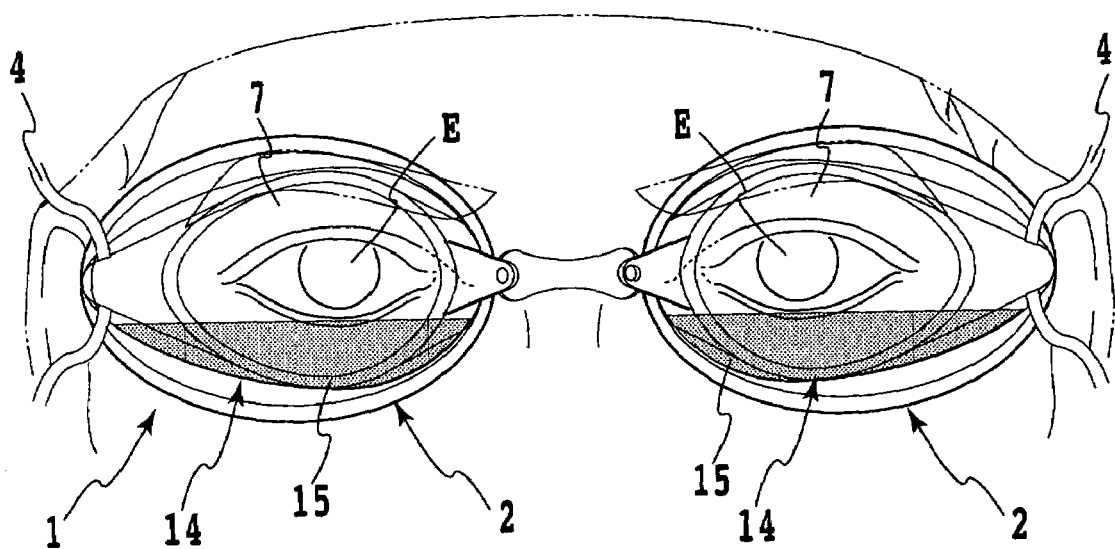
FIG. 13 is a front view showing the relevant part of FIG. 9.

More particularly, as shown in FIG. 1, FIG. 12 and FIG. 13, the difficult-viewing section 14 can be formed by coloring 15. In this case, the coloring 15 is not particularly limited, and can be any color.

Figure 7:
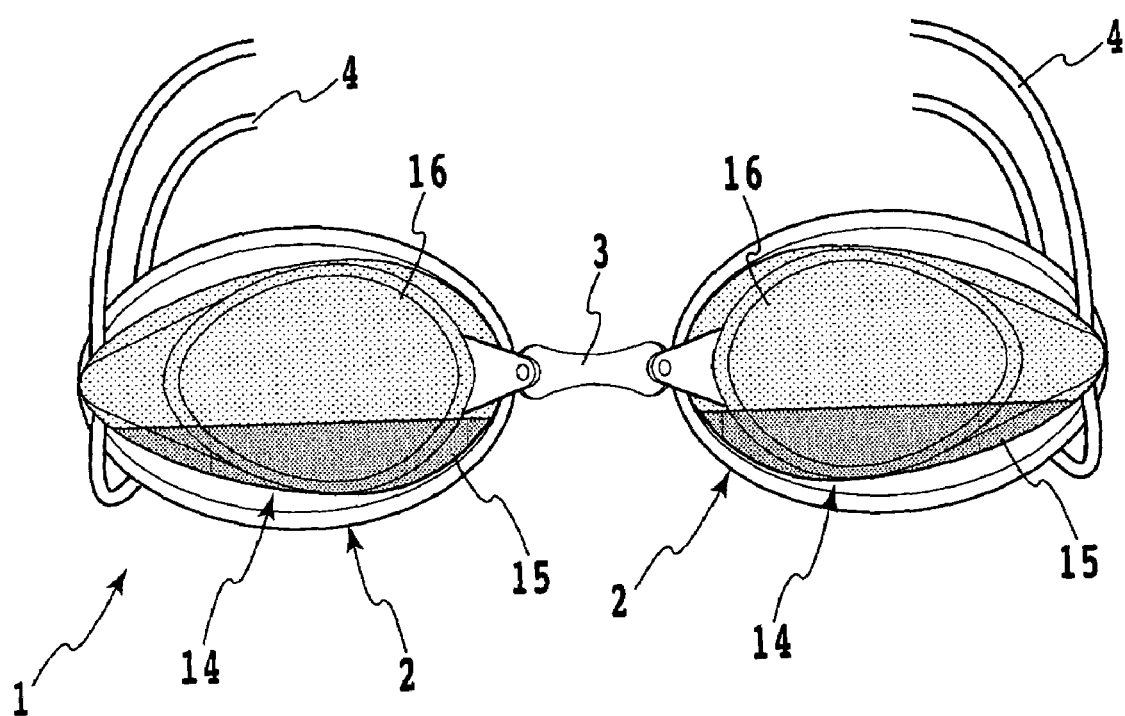
FIG. 7 is front view showing another example of the difficult-viewing section of the invention.

Also, as shown in FIG. 7, together with performing coloring 15 to form a difficult-viewing section 14, it is possible to perform coloring 16 of the eyecup 2 in the part other than the difficult-viewing section 14 (must include the forward-viewing section 7) that is easier to see through than the coloring 15. In that case, the color 15 of the difficult-viewing section 14 and the color 16 of parts other than the difficult-viewing section 14 can be the same color or different colors.

Figure 8:
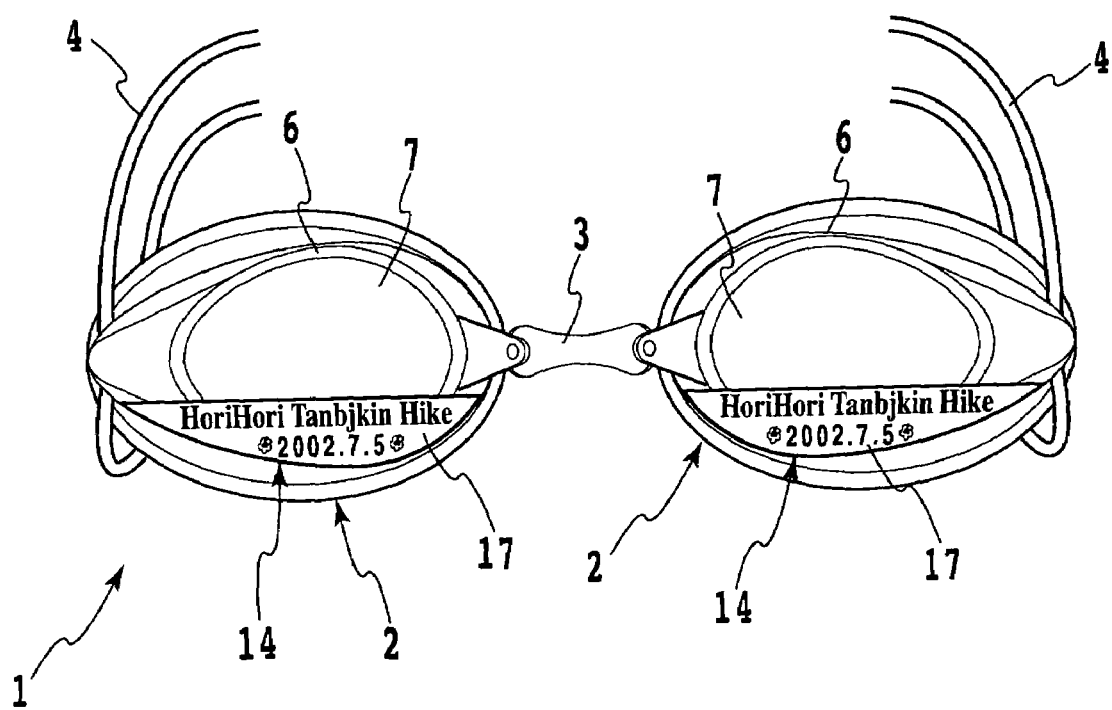
FIG. 8 is front view showing another example of the difficult-viewing section of the invention.
Figure 9:
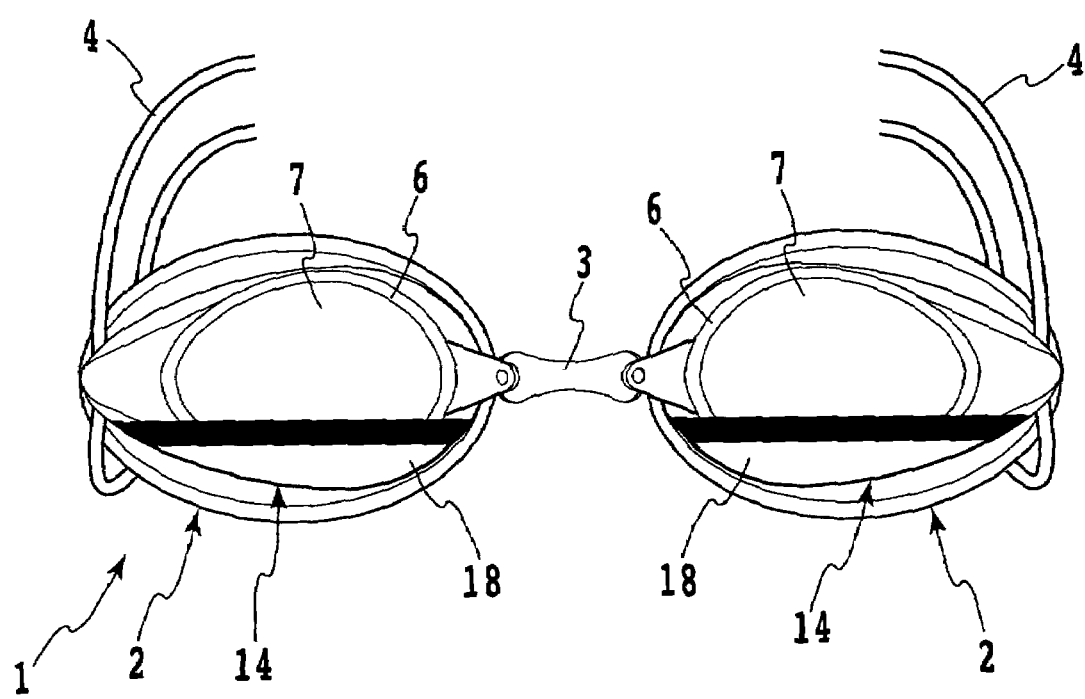
FIG. 9 is front view showing another example of the difficult-viewing section of the invention.
Figure 10:
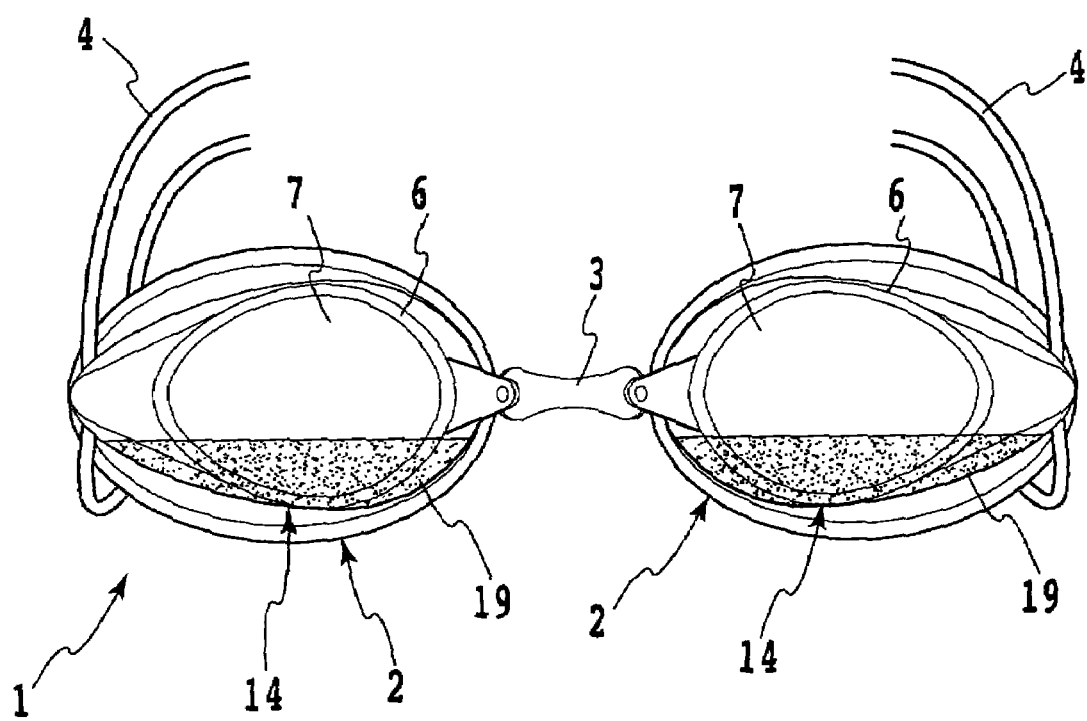
FIG. 10 is a front view showing another example of the difficult-viewing section of the invention.
Figure 11:
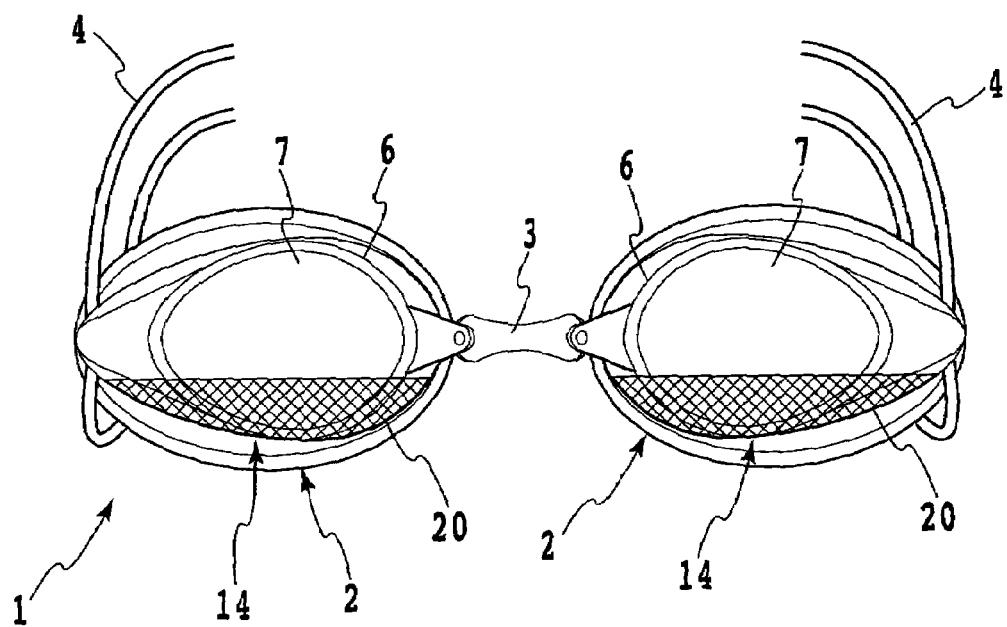
FIG. 11 is a front view showing another example of the difficult-viewing section of the invention.

Moreover, as shown in FIG. 8, it is possible to use text 17 to form the difficult-viewing section 14. Furthermore, as shown in FIG. 9, it is possible to perform gradation 18 to form the difficult-viewing section 14. Also, as shown in FIG. 10, it is possible to use a pattern 19 to form the difficult-viewing section 14. Moreover, as shown in FIG. 11, it is possible to use mesh shading 20 to form the difficult-viewing section 14. Furthermore, it is also possible to use a mirror coating or texturing.

The method for forming the difficult-viewing section 14 is not particularly limited, and any method can be used; for example, when the forward-viewing section 7 and peripheral section 6 are formed into one piece, it is possible to use coloring 15, 16, patterning 19, graphic images, text 17, gradation 18, mesh shading 20 or the like in just one desired location. Also, when forming the forward-viewing section 7 and peripheral section 6, it is possible to form them by layering a layer of the difficult-viewing section 14 such as coloring 15, 16, patterning 19, graphic image, text 17, gradation 18, mesh shading 20 or the like on top. Moreover, it is also possible to apply the coloring 15, 16, patterning 19, a graphic, text 17, gradation 18, mesh shading 20 or the like as a sticker. It is also possible to use mirror coating or texturing.

By making the swimming goggles 1 of this invention in this way, it is possible to improve the field of vision.

In other words, when swimming crawl particularly, the eyes look upward to see in the forward swimming direction. In this case, when the field of vision is inclined with respect to the forward-viewing section rather than being orthogonal, light refraction may be sensed, and it is possible that the field of vision will become poor. As shown in FIG. 2 thru FIG. 6, with the swimming goggles 1 of this invention, the top end section of the forward-viewing section 7 (main-viewing section 9) is located around or near the contact section 5 of the eye cup 2. Since the forward-viewing section 7 (main-viewing section 9) extends to or near the contact section 5, the forward-viewing section 7 (main-viewing section 9) is such that the top is inclined in the direction backward from the viewing direction. The field of vision when the eyes are looking upward is in a direction that is orthogonal or nearly orthogonal with respect to the forward-viewing section 7 (main-viewing section 9). Therefore, there is no feeling or very little feeling of light refraction, and viewing in the upward direction becomes good. Therefore, it is possible to improve the field of vision and especially improve the field of vision in the upward direction.

Figure 14:
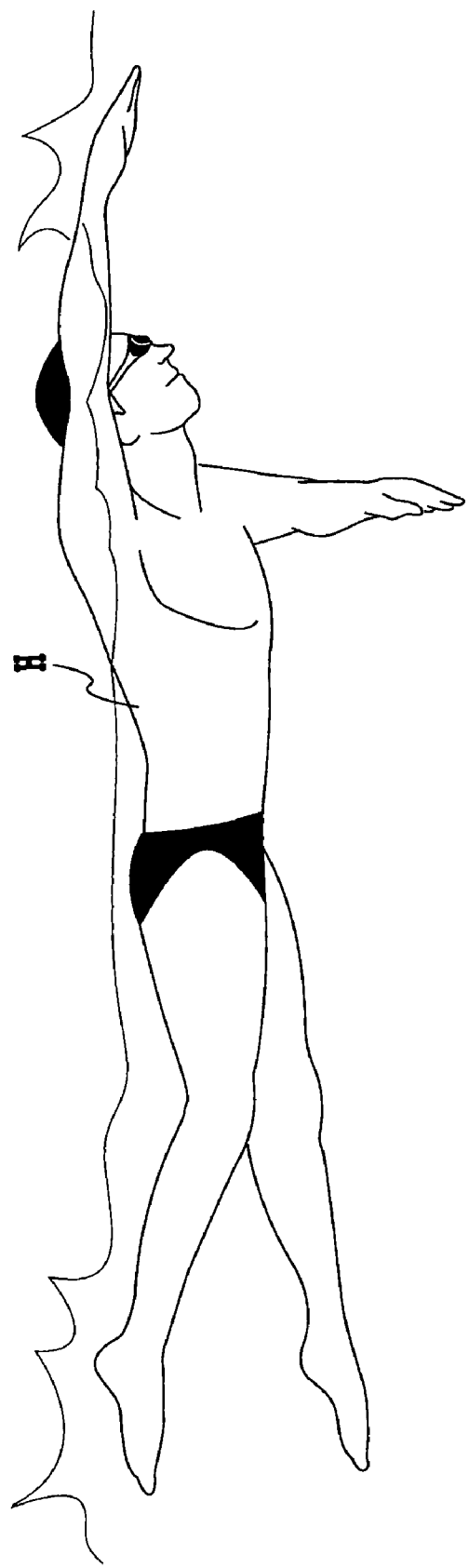
FIG. 14 is a side view showing a swimmer that is swimming crawl.

As shown in FIG. 14 when the swimming goggles 1 are worn and the swimmer is swimming crawl, the field of vision in the forward direction is good (the top of the goggles 1), so it is possible to look forward by simply moving the eyes, and thus form is inevitably improved, resulting in improved time. Also, even in a crowded pool the field of vision is enlarged, so it becomes possible to swim at ease without bumping into other people. Since it is possible to maintain safety at the same time, the practical effect is very large.

Also, the swimming goggles 1 of this invention have a difficult-viewing section 14, so it further becomes possible to swim without feeling light refraction.

In other words, for example, when the swimmer wears swimming goggles (goggles not having a difficult-viewing section 14) that are formed such that the forward-viewing section 7 comprises a main-viewing section 9 and vertical section 11 and swims crawl as shown in FIG. 14. When doing this, the swimmer swims looking forward with just the eyes looking up, and mainly uses just the main-viewing section 9, so there is hardly any problem. However, when swimming in an up and down motion such as when swimming breaststroke or butterfly, it possible that the swimmer will look through both the main-viewing section 9 and vertical section 11. For example, some swimmers will use the main-viewing section 9 when lifting the face out of the water, and use the vertical section 11 when in the water. In this case, when viewing separately through the main-viewing section 9 and vertical section 11, there is no real problem. However, when looking through the main-viewing section 9 and vertical section 11 at the same time, or when looking through the border section 12 between them, the inclination angle of main-viewing section 9 and vertical section 11 differ, so light refraction is different and what is seen appears to be different. For example, when looking through the vertical section 11, the light refraction is felt, and things appear more curved than when looking through the main-viewing section 9. Therefore, two images having different degrees of curvature are seen, and it is possible that the swimmer may become nauseous.

Also, when bending and turning the body as when making a turn, nearly the entire eyecup 2 is used, so two images having different degrees of curvature are seen, and there is a possibility that the swimmer may become nauseous or dizzy.

Moreover, when there are lines drawn on the bottom of the pool and the swimmer looks at those lines when swimming, there is no problem as long as there are no other lines except those on the bottom. However, when the bottom has seams such as grid lines made by the laid tiles, the lines may appear to bend.

Therefore, as shown in FIG. 1 thru FIG. 13, by forming a difficult-viewing section 14, when there is a part that is easy to look through (the portion of the forward-viewing section 7 where the difficult-viewing section 14 is not formed in the examples shown in FIG. 2, FIG. 4 and FIG. 6, or the main-viewing section 9 in the examples shown in FIG. 3 and FIG. 5) and a part that is difficult to look through (difficult-viewing section 14), a person will inevitably use the part that is easy to look through. Particularly, while swimming, the swimmer uses the part that is easy to look through, and no longer looks through the main-viewing section 9 and vertical section 11 at the same time or looks through the border 12 between them, so it is possible to swim without feeling the light refraction.

Moreover, by forming a difficult-viewing section 14, the swimmer tries to more effectively use the main-viewing section 9 in order to maintain the forward field of vision while swimming, so the swimmer swims using just the main-viewing section 9. That is, the swimmer understands (realizes) naturally without having to explain the correct direction to look in order to maintain the forward field of vision.

Figure 16:
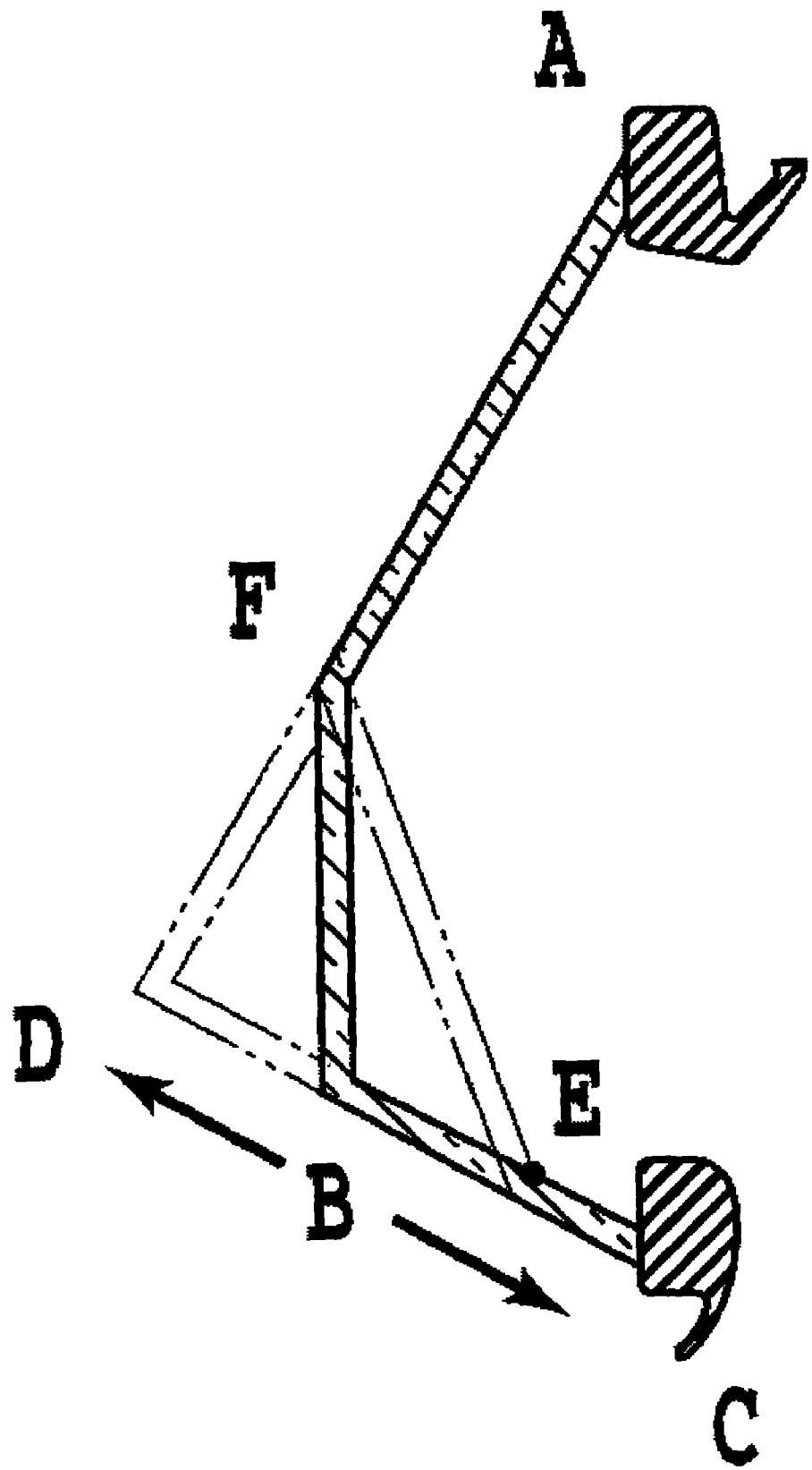
FIG. 16 is a vertical cross-sectional view showing the swimming goggles of another embodiment of the invention.

Furthermore, as shown in FIG. 16, the vertical section FB can also be inclined within the range FB to FD (a), or FB to FE (b) (E is the center of the peripheral section BC).

INDUSTRIAL APPLICATION

With this invention, together with being able to obtain swimming goggles that are capable of improving the field of vision, it becomes possible for the swimmer to swim without feeling the light refraction.

What is claimed is:

1. Swimming goggles having a pair of left and right eye cups comprising: a contact section that comes in contact with the area surrounding the eye; a peripheral section that is located around that contact section and that, when worn, extends a specified distance forward in the viewing direction; and a forward-viewing section that is arranged on that peripheral section; and where the length in the viewing direction of the top part of said peripheral section is formed such that it is shorter than the other parts of said peripheral section; and a difficult-viewing section is located at the bottom part of said forward-viewing section such that it is more difficult to see through than the top portion of said forward-viewing section.

2. The swimming goggles of claim 1 wherein said forward-viewing section comprises: a vertical section that extends a specified distance upward from the bottom end section to a position below the center position; and a main-viewing section that is inclined from the vertical section in the backward direction from the viewing direction to or near said contact section.

3. The swimming goggles of claim 2 wherein the border between said vertical section and said main-viewing section is curved.

4. The swimming goggles of claim 2 wherein said difficult-viewing section is located on all of said vertical section.

5. The swimming goggles of claim 2 wherein said difficult-viewing section is located on part of said vertical section.

6. The swimming goggles of claim 5 wherein said difficult-viewing section is formed by using coloring, patterning, graphic images, text, gradation, mesh shading, mirror coating, texturing, semi-transparency or a combination of these.

7. The swimming goggles of claim 5 wherein said difficult-viewing section is formed using coloring, and said forward-viewing section is formed such that it is the same color as or a different color than said difficult-viewing section, and that the color is easier to see through than that of said difficult-viewing section.

8. The swimming goggles of claim 5 wherein said difficult-viewing section is formed such that it is colored, and said forward-viewing section is transparent.

9. The swimming goggles of claim 8 wherein when forming said eyecup with a mold, the color of said difficult-viewing section and the color of said forward-viewing section are formed at the same time.

10. The swimming goggles of claim 8 wherein said difficult-viewing section is formed separately, and then fitted over said eyecup.

11. The swimming goggles of claim 10 wherein said difficult-viewing section is located below the center position of said forward-viewing section.

12. The swimming goggles of claim 11 wherein said difficult-viewing section is located on at least the bottom part of said peripheral section.

13. The swimming goggles of claim 12 wherein said vertical section is inclined.

14. The swimming goggles of claim 1 wherein said forward-viewing section is formed into a curved shape.

15. The swimming goggles of claim 1 wherein the border between said peripheral section and said forward-viewing section is curved.

16. Swimming goggles having a pair of left and right eye cups comprising: a contact section that comes in contact with the area surrounding the eye; a peripheral section that is located around that contact section and that, when worn, extends a specified distance forward in the viewing direction; and a forward-viewing section that is arranged on said peripheral section; and where the top end section of said forward-viewing section is formed such that it is located near said contact section; and a difficult-viewing section is located at the bottom part of said forward-viewing section such that it is more difficult to see through than the top portion of said forward-viewing section.

17. Swimming goggles having a pair of left and right eye cups comprising: a contact section that comes in contact with the area surrounding the eye; a peripheral section that is located around that contact section and that, when worn, extends a specified distance forward in the viewing direction; and a forward-viewing section that is arranged on said peripheral section; and where the top end section of said forward-viewing section is directly connected to said contact section; and a difficult-viewing section is located at the bottom part of said forward-viewing section such that it is more difficult to see through than the top portion of said forward-viewing section.

* * * * *